(12) United States Patent
Landis

(10) Patent No.: US 6,549,136 B2
(45) Date of Patent: Apr. 15, 2003

(54) SENSING AND SWITCHING CIRCUIT EMPLOYING A POSITIVE-TEMPERATURE-COEFFICIENT SENSING DEVICE

(75) Inventor: Donald G. Landis, deceased, late of Hollis, NH (US), by Sally A. Landis, administratrix

(73) Assignee: Lansense, LLC, Hollis, NH (US)

( * ) Notice: Subject to any disclaimer, the term of this patent is extended or adjusted under 35 U.S.C. 154(b) by 47 days.

(21) Appl. No.: 09/950,506

(22) Filed: Sep. 13, 2001

(65) Prior Publication Data

US 2003/0048190 A1 Mar. 13, 2003

(51) Int. Cl.[7] .............................................. G08B 21/00
(52) U.S. Cl. ....................... 340/603; 340/604; 340/618; 340/622; 73/73; 73/75; 338/22 R; 338/13
(58) Field of Search .................................. 340/603, 604, 340/618, 622; 73/73, 75; 338/22 R, 13

(56) References Cited

U.S. PATENT DOCUMENTS

| 4,031,499 A | | 6/1977 | Brueckner | 338/23 |
|---|---|---|---|---|
| 4,647,919 A | * | 3/1987 | Wright et al. | 340/608 |
| 4,656,464 A | * | 4/1987 | Cliffgard | 340/622 |
| 4,890,494 A | | 1/1990 | Osbond et al. | 73/338 |
| 5,339,689 A | * | 8/1994 | Hegge | 73/295 |
| 5,369,396 A | * | 11/1994 | Kurata et al. | 340/623 |
| 5,402,111 A | | 3/1995 | Hubbard, Jr. | 340/608 |
| 5,805,393 A | * | 9/1998 | Thomas | 361/6 |
| 6,373,347 B1 | * | 4/2002 | Cogan | 333/81 |
| 6,411,192 B1 | * | 6/2002 | Landis | 338/25 |

OTHER PUBLICATIONS

Supplemental Catalog—Keystone Thermometrics Corp. St. Mary's, Pennsylvania 1996 pp. 31 through 38.

* cited by examiner

Primary Examiner—Julie Lieu
(74) Attorney, Agent, or Firm—Robert G. Crooks

(57) ABSTRACT

A sensor and associated circuitry for sensing and reacting to the presence of a fluid or other material having heat capacity. A positive-temperature-coefficient device initiates a switching step when the amount of heat-capacity material reaches a certain level, or is totally absent. The switching step may trigger an alarm or control circuit to rectify the fluid level.

27 Claims, 11 Drawing Sheets

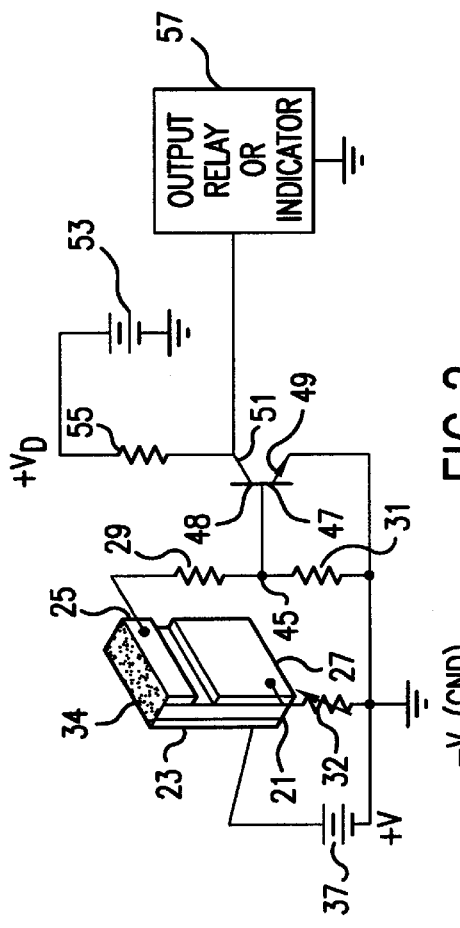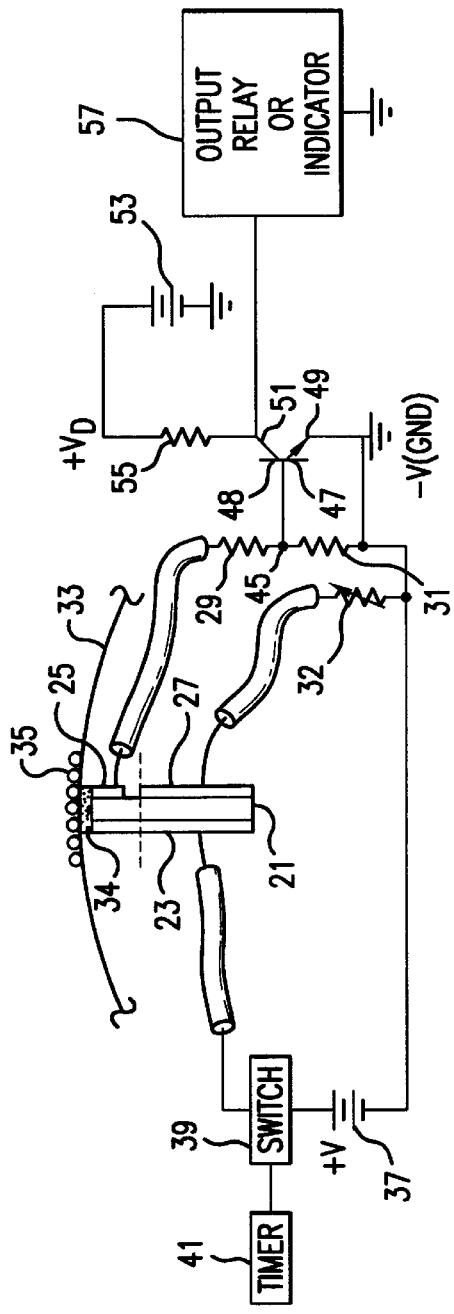
FIG.2
FIG.3

PLAN VIEW

END VIEW

SENSING AND SWITCHING CIRCUIT EMPLOYING A POSITIVE-TEMPERATURE-COEFFICIENT SENSING DEVICE

BACKGROUND OF THE INVENTION

1. Field of the Invention

This invention relates to a sensor and associated circuitry for sensing and reacting to the presence of a fluid, a permeable medium, a fluid carried by a solid medium, or other substance having heat capacity, and to a method for using the sensor and associated circuitry. It also relates to an apparatus and method for performing a switching step when the amount of the fluid or other substance, or the concentration or flow rate of the fluid, reaches a certain predetermined level.

Typical applications of the invention are as follows:
(a) Detecting the presence of rainfall or dispensed water upon an area of land served by an irrigation system;
(b) Sensing and reacting to leakage, spillage or overflow of oil within a wall surrounding an oil-storage tank;
(c) Detecting and reacting to leakage of liquid from a conduit into insulation or another substance; and
(d) Sensing and reacting to a threshold rate of flow of liquid through a conduit.

When the quantity of rainfall or dispensed water, or the spillage of oil, or the leakage of liquid, or the rate of liquid flow reaches a predetermined level, appropriate circuitry produces an electrical signal to operate an alarm or suitable control equipment as required by the circumstances.

Preferably, the sensor comprises at least one positive-temperature-coefficient ("PTC") device coupled to single or plural signal-processing circuits for actuating any desired output apparatus for indication or control.

2. Description of the Prior Art

Attention is invited to my copending application Ser. No. 09/221,733, filed on Dec. 28, 1998 and entitled "Method and Apparatus for Sensing and Measuring Plural Physical Properties, Including Temperature." That application discloses an arrangement including at least one "tablet" of positive-temperature-coefficient ("PTC") material with a plurality of zones, which have some electrical dependence upon each other. The arrangement permits the measurement of at least one physical property, one of which may be temperature.

If a property, or the presence of a substance, is to be sensed, but not necessarily measured, the circuitry may be simpler and less expensive than that which is illustrated in the aforementioned copending application. Such a less-expensive configuration is disclosed and claimed in the present specification.

Typically, PTC material comprises a mixture of barium and/or strontium titanates suitably "doped" with certain trivalent or pentavalent elements which serve to adjust the temperature at which the material reaches its "Curie point." At about the Curie point, a plot of electrical resistance of the material as a function of its temperature becomes very steep as temperature increases further. At still higher temperatures, the plot levels off at a "knee" as shown in FIG. 1 of the drawings of this specification. The characteristics of PTC materials are well described in the 1996 Supplemental Catalogue of Keystone Thermometrics, of St. Mary's, Pa., a copy of which is made a part of the file of this specification. The most pertinent disclosures appear on pages 31 through 38 of the Catalogue.

An "Atmospheric Sensor" employing PTC material is shown and described in U.S. Pat. No. 4,890,494—Osbond et al, which is also entered in the file of this specification. That patent discloses a probe of PTC material for measuring the liquid content of a gas. But it makes no mention of a switching circuit for turning on or off an indication or function. Furthermore, Osbond et al do not reveal a sensor which may comprise a single tablet of PTC material divided into zones which are nevertheless electrically and thermally dependent upon each other.

SUMMARY OF THE INVENTION

In view of the distinctions of the present invention over the prior art, I have provided a sensing and switching circuit which is new in its concept and surprising in its capabilities, while employing a modest amount of hardware.

The sensing circuit in accordance with the present invention is built around a tablet of PTC material to which are bonded, preferably on a respective first side and second side thereof, first and second layers of ohmic resistive (or conductive) material. While the first such layer is usually continuous in configuration, the second layer is separated into a first zone and a second zone which are not in direct electrically-conductive relationship with each other. The first layer is connectable, through switching or other means, to a first source of electric potential "+V." The second zone of the second layer is connected through a resistor to ground, or connected through a resistor to a second source of different electric potential.

The tablet of PTC material and the first zone of the second layer are in physical contact with a body which, from their standpoint, is a heat sink. The body may, for example, comprise a diaphragm on the opposite side of which may be present (or not be present) drops of water or other fluid. The first zone of the second layer may be electrically connected through first and second series-resistor means to ground or a source of different electric potential.

The junction or node between the first and second series-resistor means may be coupled to the input of a switching device such as an NPN transistor. The output terminals of the switching device may be connected through a gating device to an alarm, a signal light, a control valve, a motor switch, a meter, or other output device.

Means may be provided for continuously or periodically applying the voltage "+V" to the first layer of ohmic material. When the voltage "+V" is first applied to the first layer, the temperature and resistance of the tablet of PTC material are low, and the current through it immediately becomes high. But, as the current warms the tablet, the portion of it which is in contact with the second zone of the second layer reaches the Curie point and sharply increases in resistance. Accordingly, the current flowing through the second zone of the second layer and the portion of the tablet of PTC material proximate thereto will sharply decrease.

The portion of the tablet of PTC material which is in contact with the heat sink and with the first zone of the second layer of ohmic resistive material will warm up more slowly than the portion of the tablet proximate the second zone of the second layer. And if the heat sink includes a diaphragm carrying drops of water, oil, or other liquid of high heat capacity, the portion of the tablet proximate the first zone of the second layer will warm up still more slowly. The warm-up time as seen through the first zone of the second layer, when compared with the warm-up time as seen through the second zone of the second layer, will be substantially greater. Moreover, the time disparity will increase with the concentration of heat-absorbing water or oil or other material (the "heat sink") on the opposite side of the diaphragm or other structure that is in physical contact with the portion of the tablet of PTC material proximate the first zone of the second layer of ohmic resistive material.

In accordance with the present invention, the attainment and surpassing of the Curie point by the portion of the tablet of PTC material which is proximate the heat sink and the first zone of the second layer of ohmic material is an event which can initiate a switching action. When that portion of the tablet reaches the Curie point, the current through it and its associated first and second series-resistor means drops sharply, and the current available from the node between the series-resistor means becomes insufficient to maintain the transistor in its conductive state. The transistor therefore turns off. This switching action in response to the state of the heat sink is one of the most useful features of this invention.

Also in accordance with the present invention, controlled heat flow from the portion of the tablet proximate the second zone to the portion of the tablet proximate the first zone is useful in establishing the thermal and electrical conditions required for initiation of the switching action. Such controlled heat flow may be referred to as a "thermal boost."

BRIEF DESCRIPTION OF THE DRAWINGS

The invention summarized above will be described in detail in the following specification, which will be best understood if it is read while referring to the accompanying drawings, in which:

FIG. 2 is a schematic representation, partly in perspective, of the electrically-functional elements of a sensor and simple switch in accordance with this invention;

FIG. 3 is a side view, partly in section, of a sensor and switching circuit in accordance with this invention in which the portion of the tablet of PTC material proximate the first zone of the second layer of ohmic material is in physical contact with a thin diaphragm in the form of a shallow dome;

DETAILED DESCRIPTION OF THE PREFERRED MODE OF CARRYING OUT THIS INVENTION

Figure 1:
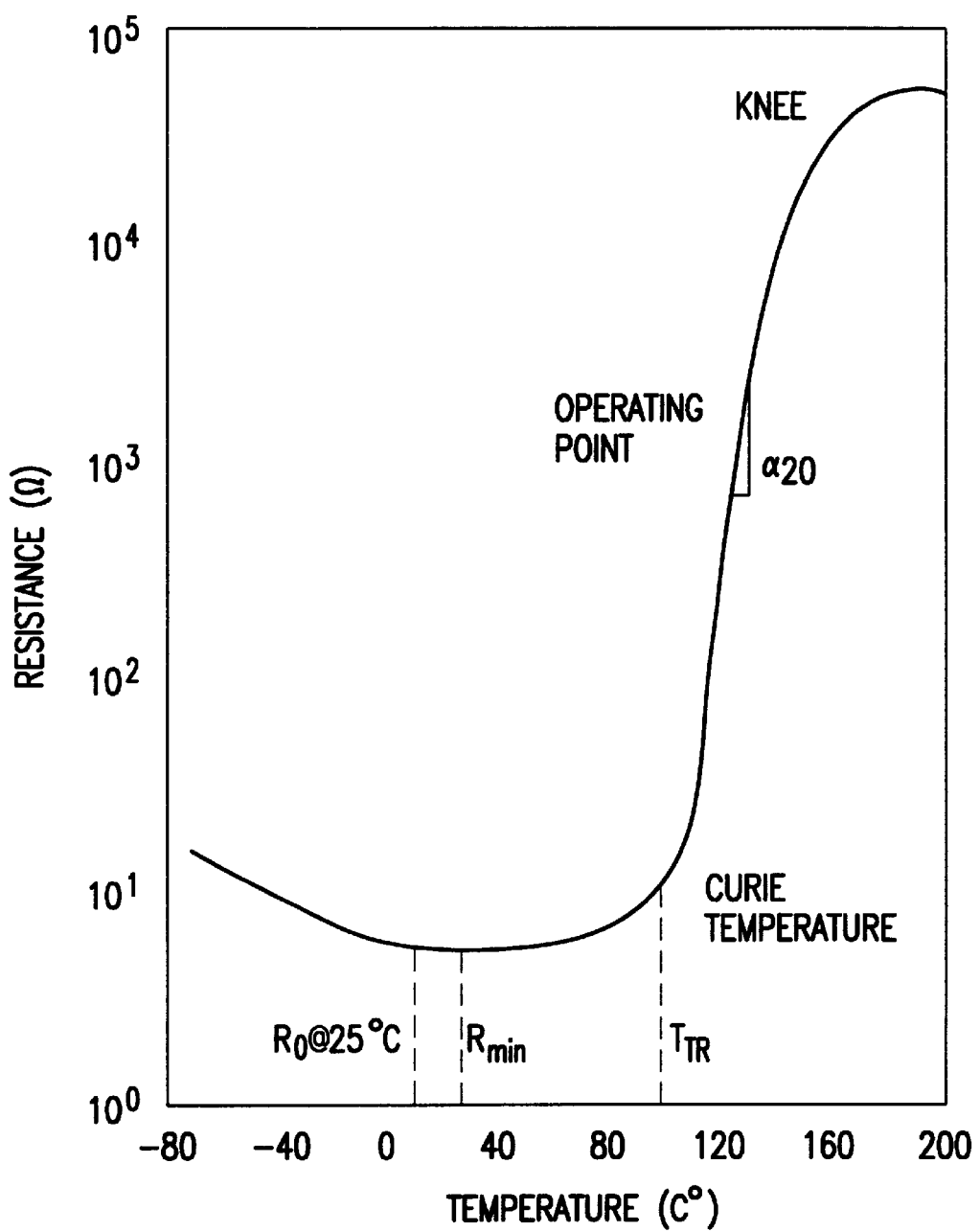
FIG. 1 is a plot of a typical relationship of electrical resistance of a PTC material as a function of its temperature, both above and below the "Curie" transition temperature.

Referring first to FIG. 1 of the drawings, we see a plot of electrical resistance, shown on a logarithmic scale, of a positive-temperature-coefficient ("PTC") material per se, as marketed commercially by the Keystone Thermometrics Company of St. Mary's, Penn., among others. The plot shows how, as temperature increases, the resistance of the material dips slightly to a minimum value and then rather suddenly increases at the transition temperature commonly known as the "Curie Temperature". And the resistance then continues to increase at a very sharp rate with respect to the corresponding increase in temperature, at least up to a rather ill-defined "knee" of the curve, where it begins to level out. Within a certain narrow temperature range, the slope of the curve of resistance as a function of temperature is so steep that one is tempted to regard it as vertical. Of course, it is not truly vertical, but nevertheless a very small change in temperature produces a very large change in resistance, which is not fully dramatized by the logarithmic scale of FIG. 1.

The PTC material is likely to be primarily barium titanate, admixed with certain other titanates and compounds which can "adjust" the position of the "Curie Temperature" from below the freezing point to well above the boiling point of water. Specifications of various PTC materials are available from Keystone and others.

Turning to FIG. 2 of the drawings, we see the electrical circuitry of a sensor and simple switch in accordance with this invention. A principal element of the sensor is a tablet 21 of PTC material, shown roughly in the configuration of a parallelepiped, which may be rounded on the top end.

PTC material is available from Keystone and others in various physical forms. Commonly, tablets of PTC material are sold in the form of a rectangular prism. Alternatively, they can be purchased in circular-cylindrical form, like "pills". In either case, the titanate composition is likely to be covered on two flat sides by respective layers of material having an ohmic characteristic so as to spread an applied electric potential evenly over the side surfaces of the PTC material. The layers of ohmic material are bonded to respective side surfaces of the tablet or pill of PTC material.

In the configuration of FIG. 2, a first layer 23 of ohmic material is bonded to a first side of tablet 21, while the second side of tablet 21 is covered, in bonded fashion, by a first zone 25 and a second zone 27 of ohmic material which are distinct from one another. The distinctness may be achieved by removing a narrow channel of the ohmic material from the continuous covering bonded to the second side of the tablet by the manufacturer.

First zone 25 is connected through a first series resistor 29 and a second series resistor 31 to ground, or to a source of preferably negative potential. Second zone 27 is connected through a third resistor 32 to ground or said source of negative potential. Series resistors 29 and 31 constitute a voltage divider. Third resistor 32 may be variable.

Figure 4:
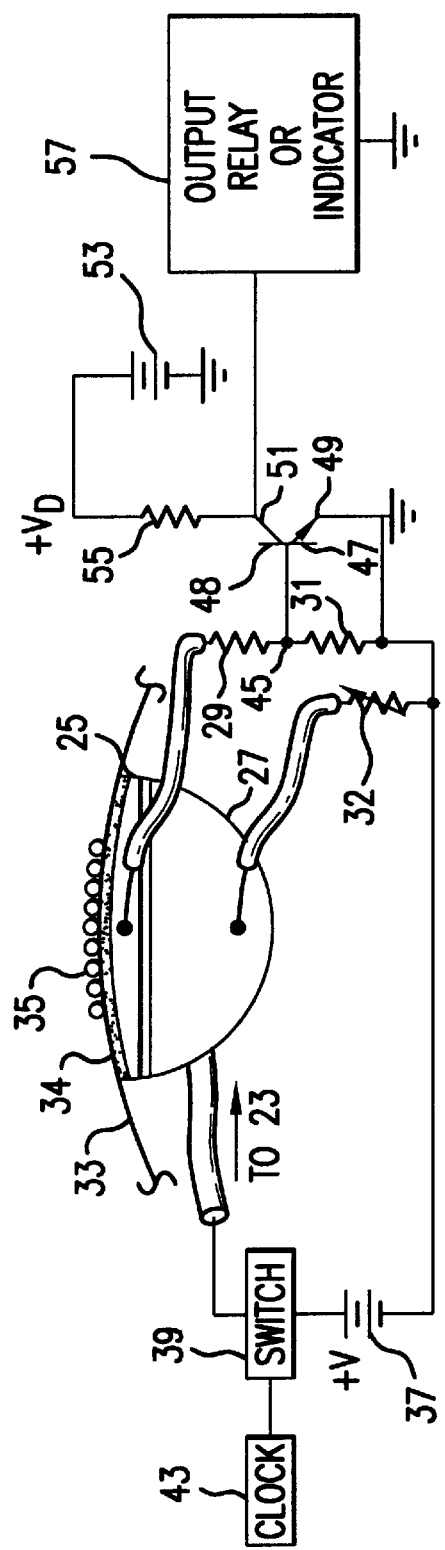
FIG. 4 is a front view, again partly in section, of the sensor and switching circuit shown in FIG. 3, similarly in contact with a shallow-dome diaphragm, and showing clearly the cut in the surface of the second layer of ohmic material that separates the first zone thereof from the second zone.

The portion of tablet 21 proximate first zone 25 of ohmic material may be placed in physical contact with any substance characterized by significant heat capacity, or specific heat. Such physical contact may be direct or through an intervening membrane such as the diaphragm 33 bonded to tablet 21 by a thin layer of thermal epoxy 34 as shown in FIG. 3 and FIG. 4 of the drawings. One of the objects of the invention is to sense the presence of a substance having heat capacity and located on the side of the membrane or diaphragm remote from tablet 21.

For the purpose of explanation, let us assume the presence of water drops 35 on top of diaphragm 33. Now, if first layer 23 is connected to a first source 37 of positive potential "+V", a first electric current will flow through first layer 23, tablet 21, first zone 25, first series resistor 29, and second series resistor 31 to ground. A second electric current will flow through first layer 23, tablet 21, second zone 27 and third resistor 32 to ground. Both currents may be initiated, if desired, by the closure of a switch 39 as shown in FIG. 3 and FIG. 4, the operation of which may be controlled by a timer 41 as shown in FIG. 3 or a clock 43 as shown in FIG. 4.

When the voltage "+V" of first source 37 is applied to first layer 23, tablet 21 is at ambient temperature. At that temperature, the resistance of tablet 21 is near its minimum value, as shown by the plot of FIG. 1. Tablet 21 is below its Curie temperature. Stated conversely, a PTC material will have been chosen for tablet 21 such that the Curie temperature of the material is appreciably higher than the temperature of the environment in which the sensor and switch of this invention are expected to be operated. As has been explained, the manufacturer can supply PTC material blended to have a Curie temperature somewhat higher than most comfortable environments. Referring again to FIG. 1, the Curie temperature of approximately 95 degrees Centigrade is appreciably higher than room temperature of about 20 degrees Centigrade.

If the sensor and switch are to operate rapidly, first source 37 may provide a voltage "+V" of approximately 24 volts. Typically, the "cold" resistance of tablet 21 is in the vicinity of 50 ohms. Accordingly, a total current of several hundred milliamperes can be expected to flow through tablet 21. But from the time of the first surge after closure of switch 39, the current density is non-uniform through the cross section of tablet 21, and it becomes more so as time passes. To a first approximation, the total current can be considered as the sum of the first current, through first zone 25, and the second current, through second zone 27.

The "$I^2R$" heating produced by the second current flowing through the end of tablet 21 proximate second zone 27 and most remote from first zone 25 causes that end of tablet 21 to warm up rapidly and soon reach its Curie temperature, whereupon its resistivity increases sharply. On the other hand, the "$I^2R$" heating produced by the first current flowing through the end of tablet 21 proximate first zone 25 produces warming more slowly; consequently that end of tablet 21 reaches its Curie temperature somewhat later. This delay is attributable to the heat flow from that end of tablet 21 through diaphragm 33 and into water drops 35. Even if the water drops were not present, the end of the tablet 21 proximate first zone 25 would probably warm up slightly more slowly than the end proximate second zone 27 because of the finite heat loss into diaphragm 33, however small.

So, the two ends of tablet 21 will attain the Curie temperature and increase sharply in resistance at different instants. In each case, the current flowing through that end of tablet 21 will decrease. The second current is determined primarily by the voltage "+V" from first source 37, the resistivity of second zone 27 and that of the portion of tablet 21 proximate second zone 27, and by third resistor 32. The second current will decrease rapidly until its portion of tablet 21 finds a stable operating point on the plot of resistance versus temperature as shown in FIG. 1. The operating point may be at the place indicated on the steep slope of that plot.

The first current, on the other hand, is determined by first series resistor 29 and second series resistor 31 as well as voltage "+V" and the resistance of first zone 25 and that of the portion of tablet 21 proximate first zone 25. As has been noted, the latter resistance is slower to increase than that of the portion of tablet 21 proximate second zone 27, and must be analyzed together with series resistors 29 and 31, whose purpose will now be explained.

The first node 45 between first series resistor 29 and second series resistor 31 may be connected to the base 47 of a first transistor 48 having also an emitter 49 and a collector 51. For the purpose of discussion, let us assume that the transistor is an NPN device, and that emitter 49 is grounded, as is the end of second series resistor 31 remote from first node 45. Then, if the voltage on base 47 is less than 0.7 or is negative, there will be no current between emitter 49 and collector 51. However, the magnitude of second series resistor 31, relative to the sum of the resistances of first series resistor 29 and cold tablet 21, is chosen so that more than 0.7 volt will appear across second series resistor 31 when switch 39 is closed and current rushes through tablet 21 in its low-resistance state. Thus, after closure of switch 39, the transistor immediately turns on.

While serving as a voltage divider determining the bias voltage on the transistor, first series resistor 29 and second series resistor 31 must also be selected to permit sufficient current to flow through first zone 25 to allow the portion of tablet 21 proximate first zone 25 to reach the Curie temperature, albeit not as rapidly as does the portion of tablet 21 proximate second zone 27. The sensitivity and response time of the sensor and switch are partially determined by choice of resistance values. And those resistance values derive their significance from the resistance of tablet 21, both below and above the Curie temperature.

In order to discuss resistances of the sensor and circuitry in a useful form, let us turn to FIG. 3 and FIG. 4 of the drawings. Those figures show, respectively in side view and front view, a tablet 21 in the configuration of a half cylinder. The half cylinder has been formed by dividing a cylinder of PTC material by a diametrical plane passing through the axis of the cylinder, and then by buffing the cut surface of one half cylinder to allow it to interface closely with diaphragm 33 in the form of a shallow dome. One suitable barium titanate product of Keystone has a diameter of 0.31 inch and an axial thickness of 0.4 inch. The channel cut through the second layer of ohmic material to separate first zone 25 from second zone 27 is shown in both figures, but is especially apparent in FIG. 4. The tablet may be adhered to diaphragm 33 by a thin layer of thermal epoxy 34.

Now, with reference to FIG. 2, FIG. 3, and FIG. 4, some typical values of the illustrated components and currents will be given. It should be remembered that the numerical values to be presented are exemplary only, and should not be interpreted in a limiting sense. It should also be borne in mind that the components and currents should be such as to allow the entire bulk of tablet 21 to reach the Curie temperature, but that the portion of tablet 21 proximate first zone 25 will be slower in attaining that temperature than the portion proximate second zone 27 if there is a significant amount of heat-capacity material in contact with diaphragm 33 or with the portion of tablet 21 proximate first zone 25.

Figure 9A:
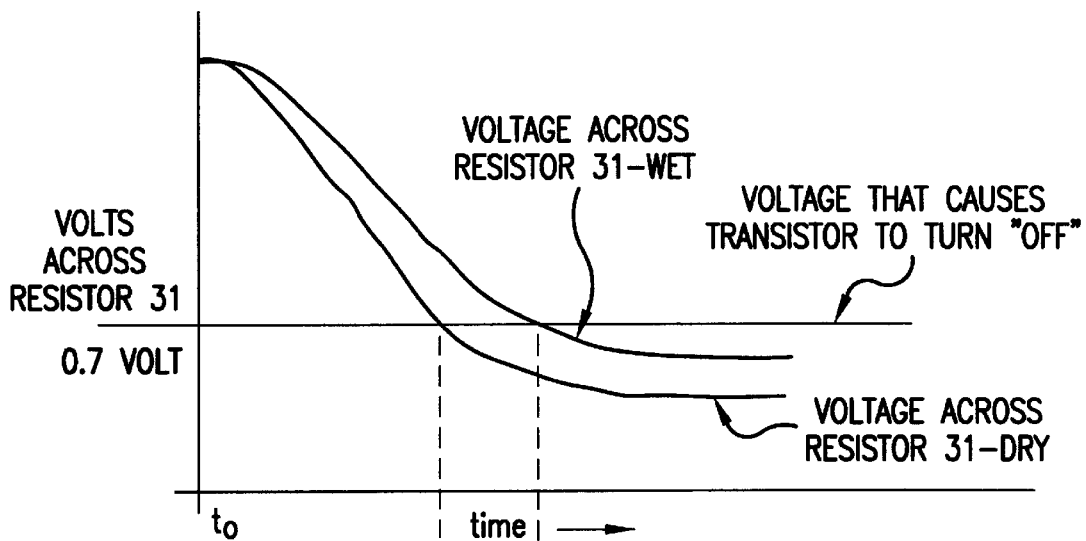
FIG. 9A is a third plot of the respective voltages across one resistor means in series with the first zone of the second layer of ohmic material as functions of time when moisture is present, and again when moisture is not present on the surface of the diaphragm of the sensor and circuit illustrated in FIG. 3 and FIG. 4.
Figure 9B:
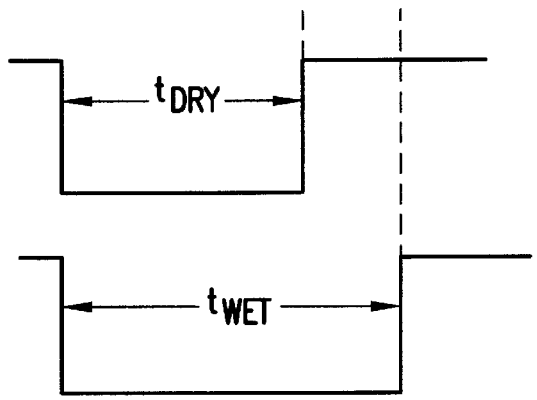
FIG. 9B is a plot, correlated in time to the plot of FIG. 9A, showing current through the collector and emitter of a transistor to the base of which, as shown in FIG. 2, FIG. 3, and FIG. 4, is fed current drawn from a node between the aforementioned resistor means, depending upon whether moisture is or is not present on the diaphragm.

After the closure of switch 39 and the initiation of current flow through tablet 21, the tablet begins to dissipate heat to its environment. If the environment is simply air, as is the case with the portion proximate second zone 27, the rate of heat dissipation is relatively low. But if drops of water or other heat-capacity material are present on the diaphragm, the rate of heat dissipation from the portion proximate first zone 25 will be somewhat higher. Consequently, the rate of build-up of temperature in that portion of tablet 21 will be lower, the Curie temperature will be attained later, and the attenuation of current through first zone 25, first series resistor 29, and second series resistor 31 will be somewhat delayed. Accordingly, the turn-off of the transistor is likewise delayed, as clearly illustrated in FIG. 9A and FIG. 9B. The length of the delay is a measure of the amount of water, or other heat-capacity substance, which is present on the surface of diaphragm 33. The amount of delay produced by the heat capacity of the diaphragm itself can be taken into account in the calibration of the sensor and switch. Let us next consider another illustrative example, including representative numbers which, again, are not to be taken in a limiting sense.

A. Rain Detector

The circuitry described in general terms in the foregoing paragraphs may be employed in a useful device such as a rain detector or liquid-presence detector. In order to do so, collector 51 of first transistor 48 is connected through a fourth resistor 55 to a second source 53 of positive potential $V_D$, which should preferably be characterized by a stable voltage. Collector 51 may be also connected to an input terminal of an output relay or indicator 57 for registering changes in the conductive state of first transistor 48. Such changes in state of first transistor 48—from conducting to non-conducting, or from non-conducting to conducting— are occasioned by the changes in loading of diaphragm 33 which are desired to be sensed by the circuitry in accordance with this invention. The circumstances of such changes in transistor state resulting from changes in diaphragm loading will now be explained in detail. The concept of "thermal boost," which is one of the important features of the invention, will also be introduced and explained.

The sensor for use in a rain detector may be built around a tablet 21 of PTC material formed by taking one half of a Keystone disk type #RL 3006-507025-PTO, which has a diameter of 0.31 inch. The disk is divided along an axial plane passing through its center. A layer of ohmic material is bonded to each of the flat faces of the disk. The depth or thickness of each half may be approximately 0.4 inch. The planar surface formed by dividing the disk into halves may be buffed so that it can fit snugly against the concave surface of a membrane or diaphragm 33 which is slightly arched. A cut is made through the layer of ohmic material on one face of tablet 21 about 0.05 inch away from the surface formed by dividing the disk. Thus, that layer of ohmic material is divided into a first zone 25 and a second zone 27 which are not in direct electrical or thermal contact with each other. A typical configuration of tablet 21, including representative dimensions, is illustrated in FIG. 14B. Once again, the dimensions are not to be taken in a limiting sense.

Figure 5:
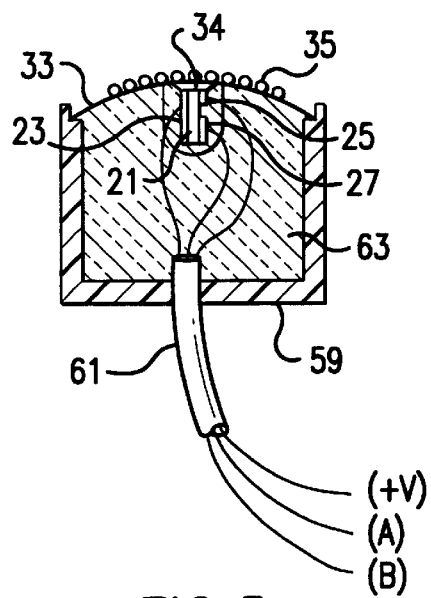
FIG. 5 is a is a side view, similar to FIG. 3 and depicted partly in section, of a sensor and diaphragm heat sink in accordance with this invention, in which the sensor has been partially enclosed in a rigid foam having some thermal conductivity so that the portion of the sensor remote from the diaphragm heat sink is thermally loosely coupled thereto in order to achieve temperature compensation of the sensor, and in which the sensor, diaphragm heat sink, and rigid foam are supported by a cup.

The buffed surface of tablet 21 may be bonded to the concave surface of diaphragm 33 by a thin layer of thermal epoxy 34. Diaphragm 33 may, for instance, be formed of nylon 0.020 inch thick and one inch in diameter. Diaphragm 33 may be fitted into a groove within the lip of a container 59, which may have a cylindrical or other easily-formed shape. Respective wires or other electrical conductors may be attached to first layer 23 of ohmic material and to first zone 25 and second zone 27 of the second layer of ohmic material. Those wires may be combined into a first cable 61 brought out through a hole in container 59 as shown in FIG. 5 of the drawings. The space in the cavity of container 59 not occupied by tablet 21 and the ohmic material and wires may be filled with rigid foam 63. The foam may be thermally insulating, Alternatively, and for reasons which will be explained later in this specification, foam 63 may be constituted by a material having a low thermal conductivity.

The cold resistance of the aforementioned disk of PTC material is about 50 ohms. When the disk is divided into two tablets 21, the cold resistance of each of the tablets 21 is approximately 100 ohms. The effective resistance of the small portion of the tablet 21 proximate first zone 25 of ohmic material is in the neighborhood of 500 ohms. The resistance of second zone 27 of ohmic material and of the portion of tablet 21 proximate second zone 27 is about 125 ohms. The resistance of third resistor 32, which connects second zone 27 to ground, may be selected from a low range such as between five and fifteen ohms. Let us assume that it is ten ohms, and that the current through it is less than one hundred milliamperes so that the voltage across third resistor 32 will be less than one volt.

Although the resistance of third resistor 32 is deliberately maintained low, the total resistance of the series combination of first series resistor 29 and second series resistor 31 may be of the order of 120 ohms—considerably higher than third resistor 32. Inasmuch as first series resistor 29 and second series resistor 31 constitute a voltage divider, the ratio between them is important. For the sake of this illustrative embodiment, let us assume that each of those resistors is 60 ohms. The voltage appearing at first node 45, between the two series resistors, will determine the conductive state of first transistor 48 at various times during the operative cycle of the switching circuit.

First source 37 of positive potential +V may typically be between 15 and 30 volts dc. For this example, let us assume that first source 37 is 24 volts. When switch 39 is closed, the entire volume of tablet 21 is in a low-resistance condition. Accordingly, if no water or other heat-capacity material is present on the upper surface of diaphragm 33, current rushes through both the portion of tablet 21 proximate first zone 25 of ohmic material and the portion of tablet 21 proximate second zone 27 of ohmic material. The modest voltage across third resistor 32 climbs sharply to a peak of about 0.7 volt and then subsides as the portion of tablet 21 proximate second zone 27 of ohmic material warms up past the Curie temperature and increases rapidly in resistance, thereby causing its current to decrease and the voltage across third resistor 32 to fall to a point where it approaches a steady-state low value of less than 0.3 volt. The voltage across third resistor 32 is plotted as a function of time in curve (A) of FIG. 7. For the circuit parameters assumed, the heat power dissipated in third resistor 32 as its current approaches the steady state is approximately 0.004 watt.

Now, turning to the current which rushes through the portion of tablet 21 proximate first zone 25 of ohmic material immediately upon closure of switch 39, that current develops a sharply peaked voltage across the series combination of first series resistor 29 and second series resistor 31. This voltage is much greater than even the maximum voltage developed across third resistor 32 because the sum of the series resistors is about twelve times as resistive as third resistor 32. So, even though the current through first zone 25 of ohmic material may be smaller than the current through second zone 27, the voltage across the series combination peaks at about 2.8 volts before beginning to subside as the portion of tablet 21 proximate first zone 25 of ohmic material passes the Currie temperature and begins to increase rapidly in resistance. This voltage response as a function of time is portrayed in curve (B) of FIG. 7.

If considerable time passed with no supervening event, the voltage across the combination of series resistors 29 and 31 would approach a steady-state value of 1.2 or 1.3 volts. In such a steady state, the current through first zone 25 of ohmic material would be about 0.01 ampere, and approximately 0.012 watt of thermal power would be dissipated to the environment and to diaphragm 33.

Figure 7:
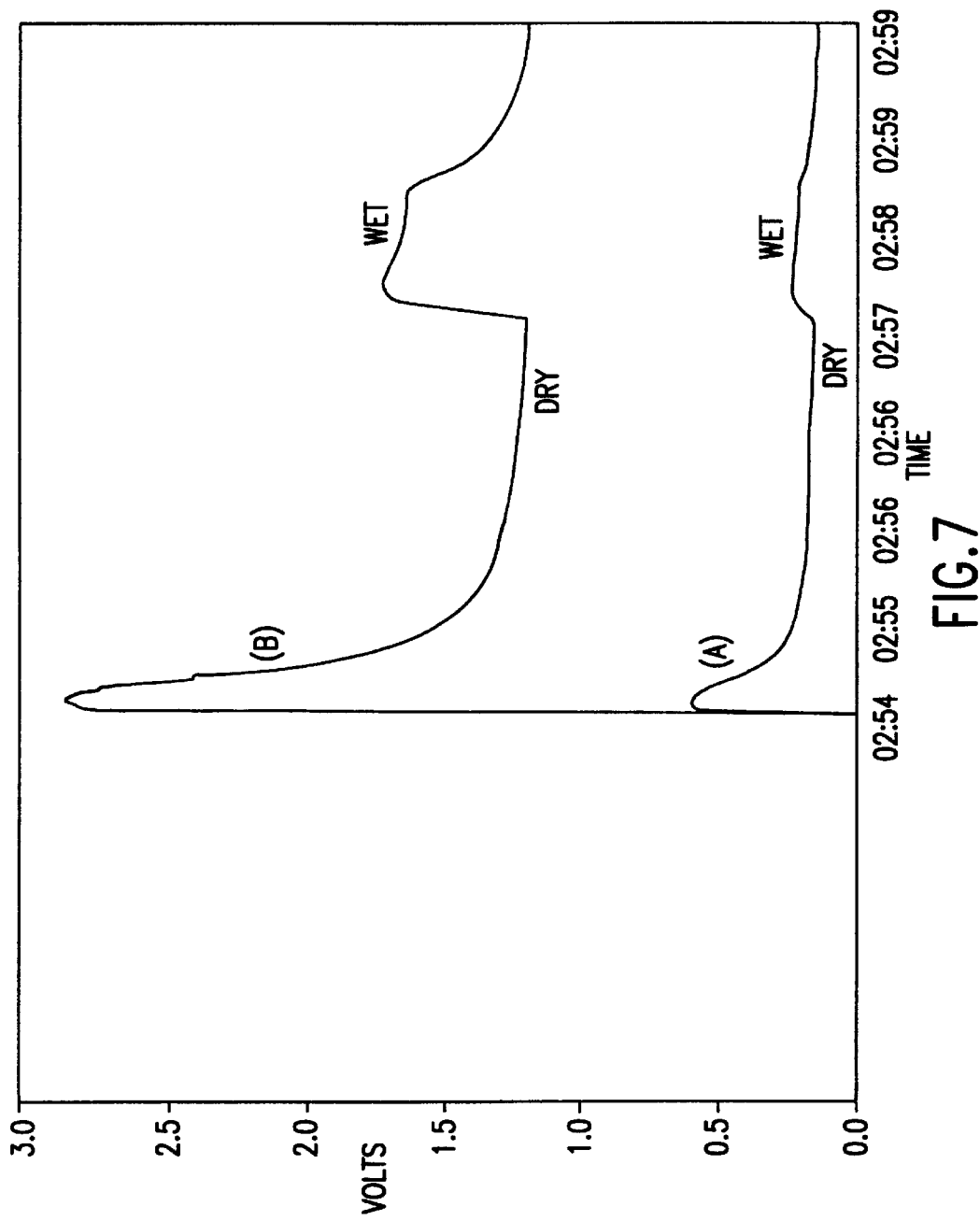
FIG. 7 is a first plot of respective voltages across resistor means in series with first and second zones of the second layer of ohmic material as functions of time as voltage is applied to the first layer of ohmic material and then as water drops are deposited on the diaphragm of the sensor illustrated in FIG. 3 and FIG. 4.

Now, if we disturb the stable operating condition by depositing a few drops of room-temperature water on the upper surface of diaphragm 33, the voltages which were approaching respective quiescent levels suddenly increase. Reference to curve (B) of FIG. 7 shows that the voltage across the series resistors 29 and 31 increases much more sharply and with much greater magnitude than the voltage across third resistor 32, as depicted in curve (A) of FIG. 7. The reason for this disparity, of course, is that the heat transferred to the drops of water from the portion of tablet 21 proximate first zone 25 of ohmic material causes the temperature of that portion to be lowered, thereby driving the operating point downward on the steep portion of the plot of FIG. 1. When that resistance sharply decreases, the current through that portion of tablet 21 increases and sharply raises the voltage across the combination of first series resistor 29 and second series resistor 31. On the other hand, the resistance of the portion of tablet 21 proximate second zone 27 of ohmic material is not so sharply decreased because that portion is not in direct thermal contact with the water on diaphragm 33.

Even with the deposit of just a few drops of water, the voltage across the series resistors jumps from about 1.2 volts to about 1.7 volts as the current goes from approximately 0.010 ampere to approximately 0.014 ampere. Consequently, the power dissipated from the portion of tablet 21 proximate first zone 25 of ohmic material goes from abut 0.012 watt for a dry diaphragm to about 0.024 watt for a slightly wet diaphragm. The difference in heat dissipation is absorbed in raising the temperature of the water.

When the water suddenly appears on the diaphragm, the voltage across the series combination of resistors goes from 1.2 volts to 1.7 volts. If the series resistors are equal in magnitude, then the voltage at first node 45 goes from 0.6 volt to 0.85 volt. If the voltage required at base 47 to turn on first transistor 48 must be at least 0.7 volt, then clearly the sharp increase in curve (B) of FIG. 7, caused by the appearance of the water, is sufficient to render first transistor 48 conductive, thereby sending a signal to operate output relay or indicator 57.

As the heat transferred through diaphragm 33 to the water thereon raises the temperature of that water, the temperature of the portion of tablet 21 proximate first zone 25 of ohmic material also rises, and the resistance of that portion of tablet 21 also increases. As that increase takes place, the current through series resistors 29 and 31 decreases, and the voltage appearing at first node 45 decreases. Reference to curve (B) of FIG. 7 shows that the voltage across the series resistors soon begins to level off, and approaches a steady state in which the voltage at first node 45 (one-half of the value indicated by curve (B)) is less than the 0.7 volt required to maintain first transistor 48 in its conductive state. Thus, the switching circuit "resets" to the state which prevailed prior to the deposit of the water drops on the diaphragm. If output relay or indicator 57 is intended merely to show that water has been deposited on the diaphragm, it will record that fact. On the other hand, if output relay or indicator 57 is intended to count the occurrences of appearance of water on the diaphragm, means must be provided to reset that indicator so that it will be ready to count the next occurrence of the deposit of water on the diaphragm. One possible application of this sensing and switching circuit would be to initiate certain action only when the number of occurrences of an event such as a shower has attained a certain predetermined level.

B. Thermal Boost

The foregoing example has posited that the sensing and switching circuit is either approaching or has attained a steady state when that near-steady state is abruptly changed by the deposit of a small quantity of water on diaphragm 33. In the steady state, the operating point of tablet 21 on the plot of FIG. 1 would be high on the steep slope of the curve. The current through series resistors 29 and 31 would be low, and first transistor 48 would not be in its conducting state. Then the heat-sinking effect of that small amount of water would suddenly lower the temperature of the portion of tablet 21 proximate diaphragm 33 and first zone 25 of ohmic material. The current through that portion of the tablet and through the series resistors would increase sufficiently to turn on first transistor 48. But, as the temperature of the small quantity of water is raised by heat transferred to it from the portion of tablet 21 abutting diaphragm 33, the operating point of that portion of tablet 21 moves back up the steep slope of the plot of FIG. 1, causing the current through the series resistors to decrease and first transistor 48 to turn off again. This is the condition that is illustrated at the right-hand end of curve (B) of FIG. 7. When the amount of water deposited onto the diaphragm is small (e.g. raindrops,) this switching back and forth of the circuitry takes place as the operating point of the portion of tablet 21 abutting diaphragm 33 moves up and down on the steep portion of the plot of FIG. 1.

Now if, instead of assuming a few raindrops falling on diaphragm 33 we assume the advent of a substantial amount of water in contact with the diaphragm, the performance of the circuit of this invention changes markedly. The change would be especially significant if the water were flowing past the diaphragm, thereby carrying away a significant amount of heat. Of course, the heat power absorbed and perhaps carried away by the water must be supplied by $I^2R$ electrical power dissipated in tablet 21. Only if the conversion of electrical energy in tablet 21 is in balance with the heat energy absorbed by the water (or other heat-sinking material on diaphragm 33) can the operating point of the portion of tablet 21 abutting diaphragm 33 be confined to short swings up and down the steep portion of the plot of FIG. 1. If the only heat were generated in the portion of tablet 21 proximate first zone 25 of ohmic material, while heat is being abstracted therefrom by lower-temperature water on the diaphragm, that portion of tablet 21 might not surpass the Curie Temperature and reach an operating point on the steep slope of the plot of FIG. 1. That portion would remain in its low-resistance state, and the current through the series resistors 29 and 31 would be so high that first transistor 48 would be "stuck" in its conducting state.

Figure 6:
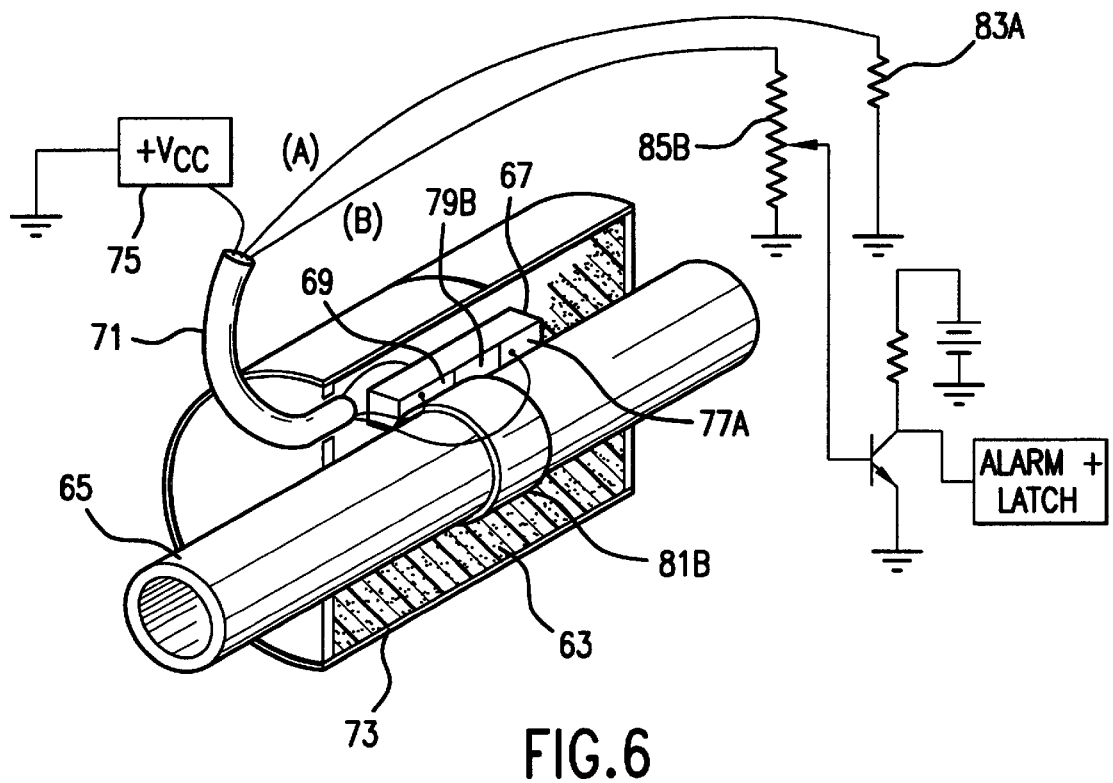
FIG. 6 is a perspective view, partly in section, of a flow-through-type leak detector mounted on a fluid conduit, in which a first zone of a layer of ohmic material on a tablet of PTC material is soldered or otherwise affixed to a metal ring encircling the fluid conduit, while a second zone of the ohmic material on the tablet of PTC material is in contact with the conduit itself.

One of the features of this invention is the "thermal boost" which is given to the portion of tablet 21 proximate first zone 25 of ohmic material by the portion of tablet 21 proximate second zone 27 of ohmic material. As shown in FIG. 5 and FIG. 6, rigid foam 63 prevents heat from radiating freely from the portion of tablet 21 proximate second zone 27 of ohmic material. Accordingly, some of the heat power generated by $I^2R$ loss in that portion flows by conduction into the portion proximate first zone 25 of ohmic material, thereby enabling it to reach and surpass the Curie Temperature even though it may be transferring heat through diaphragm 33. By adjusting the resistance of third resistor 32, as shown in FIG. 2, FIG. 3, and FIG. 4, the current flow through the portion of tablet 21 proximate second zone 27 of ohmic material may be set to maintain heat flow from that portion of tablet 21 to the portion of tablet 21 proximate first zone 25 of ohmic material to position the latter at the "threshold" of the plot of FIG. 1. This flow of heat from one portion of tablet 21 to the other may be regarded as a "thermal bias" which makes the portion abutting diaphragm 33 sensitive to small changes in the heat-sinking effect of diaphragm 33 and its burden. Thus, the thermal boost enables the switching circuit of this invention to be characterized as a "high-gain circuit."

Just as there is a temperature gradient between the two aforementioned portions of tablet 21, there is also a thermal gradient within the portion of tablet 21 proximate first zone 25 of ohmic material. And the latter thermal gradient is increased as the heat-sinking effect of the water or other burden on diaphragm 33 increases. If diaphragm 33 is made of stainless steel or some other metal, and if provision must be made for a substantial amount of water on the diaphragm, the cross-sectional area of tablet 21 in contact with diaphragm 33 may be rather small. On the other hand, if diaphragm 33 is made of plastic or some other poor conductor of heat, and if the circuitry is intended to detect the presence of but a few drops of water, the cross-sectional area of tablet 21 in contact with diaphragm 33 should be as great as possible. The embodiments of this invention which will be described in some of the following paragraphs will require especially close thermal coupling between tablet 21 and the conduit or container with which it is in juxtaposition.

C. Leak Detector

Turning to FIG. 6 of the drawings, we see a representation of a flow-through-type leak detector mounted on a fluid conduit 65. In FIG. 6, a second tablet 67 of PTC material has, on one flat surface thereof, a third layer 69 of ohmic material to which is attached a wire which is brought out in a second cable 71 through an opening in a second container 73 to a third source 75 of positive potential +$V_{CC}$. On the flat surface of second tablet 67 opposite third layer 69 of ohmic material are a third zone 77A and a fourth zone 79B of ohmic material, both bonded to second tablet 67 of PTC material but electrically separated from each other. The separation may be accomplished by forming a narrow channel in the layer of ohmic material on the tablet of PTC material as furnished by the manufacturer. A wire is attached to third zone 77A of ohmic material and is brought out of second container 73 in second cable 71. Fourth zone 79B of ohmic material is soldered or otherwise conductively affixed to the outside of a metal sleeve 81B which is in turn pressed over fluid conduit 65, thereby bringing third zone 77A into direct contact with fluid conduit 65. A wire is attached to metal sleeve 81B and is brought out of second container 73 in second cable 71.

Fluid conduit 65 may be formed of metal or a synthetic material such as Teflon brand of polytetrafluoroethylene. If fluid conduit 65 is made of plastic, it will be important to have the cross section of third zone 77A of ohmic material as large as possible in order to lower the resistance between second tablet 67 and fluid conduit 65. Second tablet 67 may be formed from a 0.31-inch-diameter Keystone disk of PTC material #3006-507025-PTO by cutting out of the disk a tablet in which the facing layers of ohmic material have the configurations of rectangles of 0.25 inch by 0.125 inch. When a narrow channel has been milled or removed from the ohmic material across the middle of one face, the remaining contact surfaces are third zone 77A of ohmic material and fourth zone 79B of ohmic material, each of which is approximately 0.12 inch square. The cold resistance of each of those zones, and of the portion of second tablet 67 proximate each of those zones, is approximately 250 ohms. A fifth resistor 83A of about ten ohms may be connected between third zone 77A of ohmic material and ground. A sixth voltage-divider resistor 85B of approximately 80 ohms may be connected between metal sleeve 81B and ground. An output-voltage tap may be placed on sixth voltage-divider resistor 85B at any desired location, such as the midpoint. The output-voltage tap may be connected to the base of an NPN transistor or other output switching device.

If, for example, the outer diameter of fluid conduit 65 is 0.25 inch, the inner diameter of metal sleeve 81B will also be 0.25 inch. Typical further dimensions for metal sleeve 81B are 0.08 inch width and 0.01 inch thickness. It may be made of brass. When the respective wires have been attached to metal sleeve 81B, third zone 77A of ohmic material, and third layer 69 of ohmic material, the assembly comprising second tablet 67 of PTC material, metal sleeve 81B, fluid conduit 65, and the three wires can be placed within the cavity formed by abutting two plastic caps to form second container 73. When the wires have been brought out in second cable 71 through a hole in second container 73, the empty space within the container may be filled with rigid foam 63.

Figure 8:
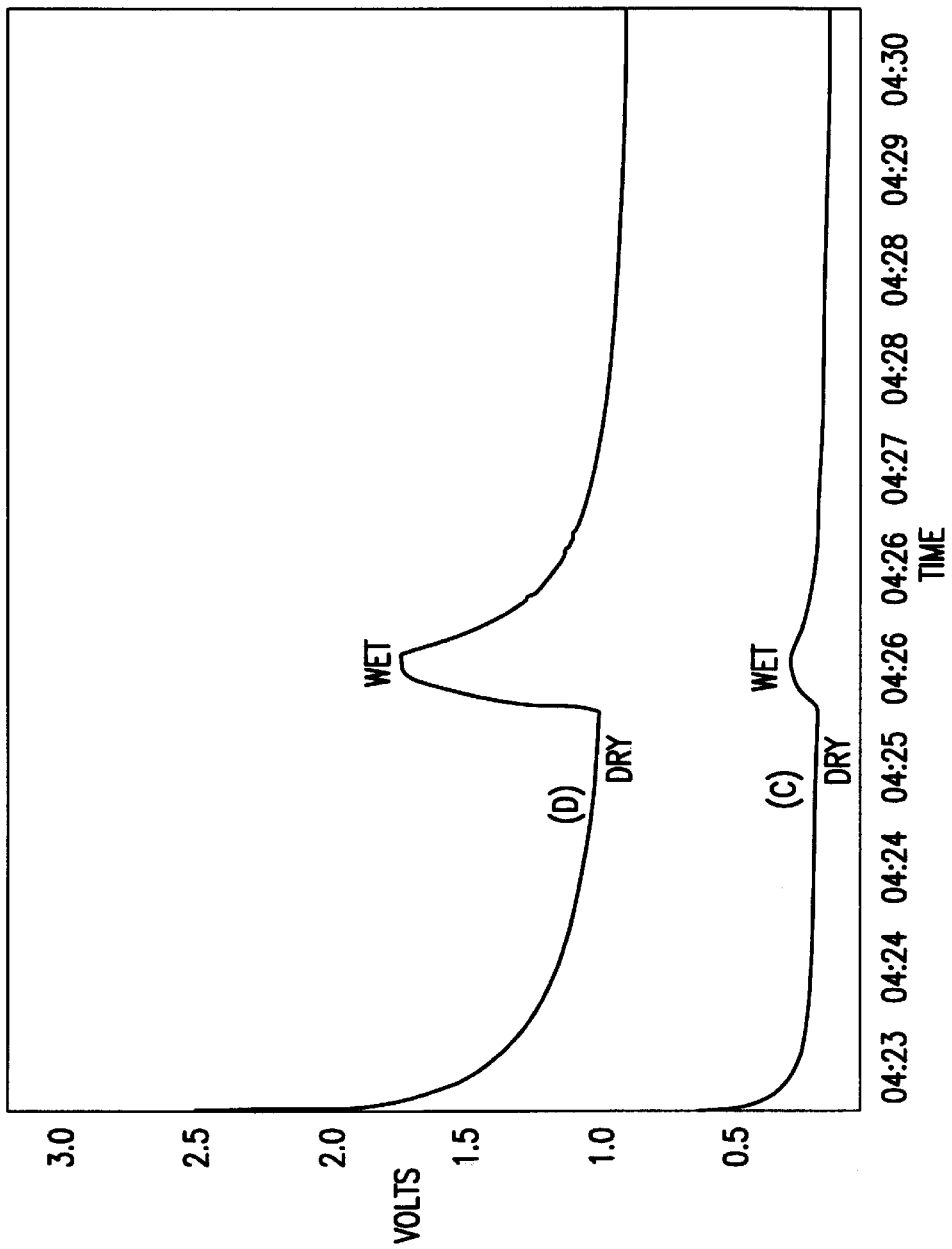
FIG. 8 is a second plot of respective voltages across resistor means in series with first and second zones of the second layer of ohmic material as functions of time as water begins to flow through the conduit of the leak detector of FIG. 6.

If a fifth resistor 83A of ten ohms is connected between third zone 77A of ohmic material and ground, and if a sixth voltage-divider resistor 85B of eighty ohms is connected between metal sleeve 81 B and ground, the performance of the leak detector will be as shown in FIG. 8 of the drawings after the initial voltage spike following energization of the circuit from third source 75 of positive potential $+V_{cc}$. As the circuit approaches the steady state with no water in fluid conduit 65, a current of about 0.02 ampere flows through fifth resistor 83A, while about 0.0125 ampere flows through sixth voltage-divider resistor 85B. The power dissipation through metal sleeve 81B and fluid conduit 65 is approximately 0.011 watt.

When water at room temperature, as from a leak, is passed through fluid conduit 65, the current through fifth resistor 83A increases to about 0.03 ampere, and the current through sixth voltage-divider resistor 85B suddenly jumps to about 0.022 ampere. The power dissipation to fluid conduit 65 and to the water then becomes approximately 0.039 watt. The voltage across sixth voltage-divider resistor 85B is then 1.75 volts. Accordingly, half of that voltage, taken from the tap on sixth voltage-divider resistor 85B, exceeds the 0.7-volt potential which is necessary to turn on the NPN transistor or other output switching device. The switching device may actuate an alarm or any other indicator, as desired. When the alarm or other indicator has been actuated, the temperature of the water may increase so much that the output voltage of the circuit decreases and stabilizes again, as shown in the right-hand portion of curve (D) of FIG. 8. A latching device may be employed so that the alarm will continue to indicate that leakage has taken place through fluid conduit 65.

D. Liquid Detector

Figure 10:
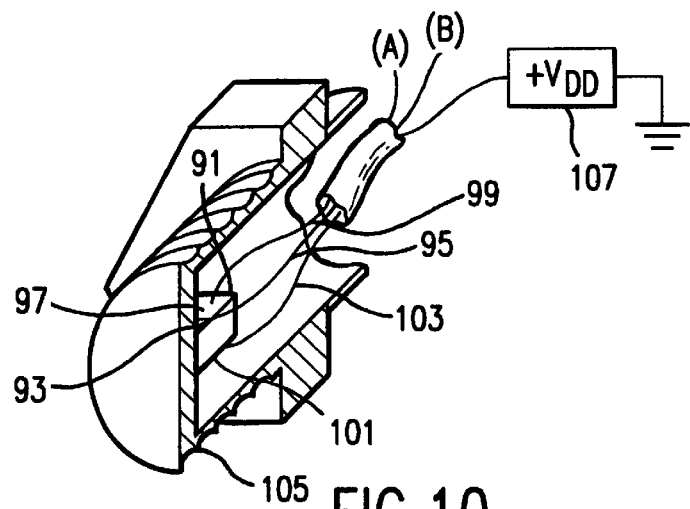
FIG. 10 is a perspective view, partly in section, of a liquid detector as shown in FIG. 2, mounted in an axial well drilled into an NPT pipe plug.

Turning to FIG. 10 of the drawings, we see a liquid detector having the circuit configuration of FIG. 2, mounted in an axial well drilled into an NPT pipe plug. As in the leak detector of FIG. 6, a third tablet 91 of PTC material may be cut out of a 0.31-inch-diameter Keystone disk. The facing layers of ohmic material may have the configurations of rectangles 0.25 inch by 0.125 inch. A narrow channel may be milled or cut across the ohmic facing layer approximately 0.08 inch from one of the narrow ends of the rectangle and parallel thereto so that a fifth zone 93 of ohmic material is formed with dimensions about 0.08 inch by 0.125 inch. A first lead wire 95 is attached to fifth zone 93 of ohmic material.

A sixth zone 97 of ohmic material remains on the same side of third tablet 91 as fifth zone 93. Its dimensions are approximately 0.125 inch by 0.16 inch. A second lead wire 99 is attached to sixth zone 97. On the other side of third tablet 91 is a seventh zone 101 of ohmic material having dimensions of 0.125 inch by 0.25 inch. A third lead wire 103 is attached to seventh zone 101. The assembly of third tablet 91 with its three ohmic zones and three lead wires is inserted into a well about one quarter inch in diameter, drilled axially into a plastic NPT pipe plug 105. The edge of fifth zone 93 of ohmic material and the portion of third tablet 91 proximate to it are thrust most deeply into the well in NPT pipe plug 105 so that the end of third tablet 91 is in contact with the bottom of the well. Third tablet 91 may be held in close contact with the bottom of the well by a thin layer of epoxy.

Seventh zone 101 is connected through third lead wire 103 to a fourth source 107 of positive potential $+V_{DD}$, which may be about 24 volts. Sixth zone 97 of ohmic material may be connected through second lead wire 99 and an external resistor of about ten ohms to ground. Fifth zone 93 of ohmic material may be connected through first lead wire 95 and a voltage-divider resistor of about 45 ohms to ground. In this configuration, in which third tablet 91 of PTC material must communicate thermally through the bottom of the well drilled into NPT pipe plug 105, there may be no need to divide the voltage developed across the resistor between first lead wire 95 and ground. Accordingly, the entire voltage developed across that resistor may be available to actuate a transistor or other switching device.

NPT pipe plug 105 may be screwed into a hole in a conduit or other vessel. When the voltage $+V_{DD}$ of fourth source 107 of positive potential is applied to seventh zone 101 of ohmic material with no water in the conduit or other vessel, the voltage across the ten-ohm resistor spikes upward to about 1.4 volts and then subsides and stabilizes as shown in curve (E) of FIG. 12. It will be understood that the voltage spikes are caused by the inrush of current before third tablet 91 of PTC material reaches and surpasses the Curie temperature. If there is no water in the conduit or other vessel, the current through the ten-ohm resistor would stabilize at about 0.04 ampere, while the current through the 45-ohm voltage-divider resistor would stabilize at about 0.028 ampere.

Figure 12:
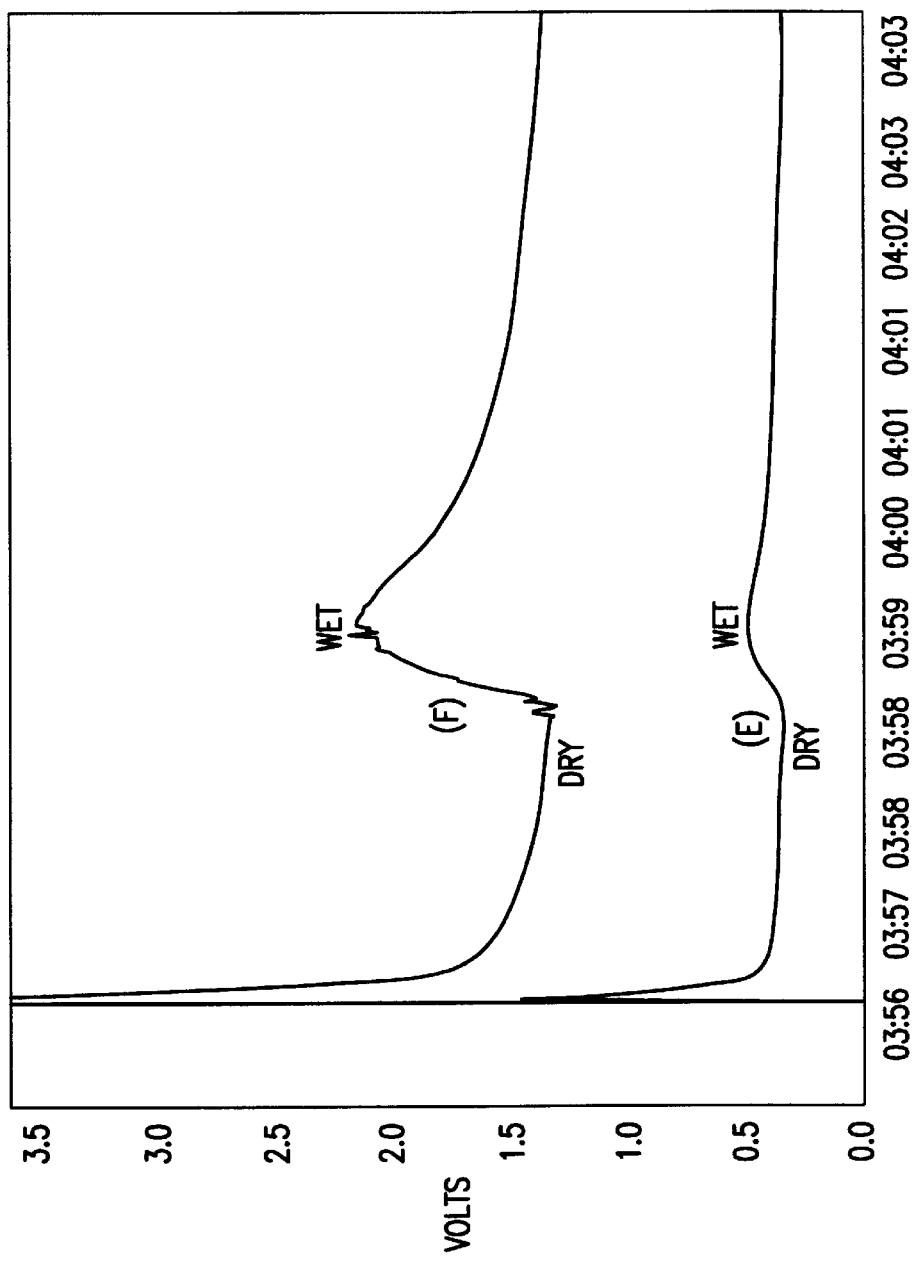
FIG. 12 is a fourth plot of respective voltages across resistor means in series with first and second zones of the second layer of ohmic material as functions of time as voltage is applied to the first layer of ohmic material and then as water starts to flow past the liquid detector of FIG. 10.

If room-temperature water appears in the conduit or other vessel and contacts the end of NPT pipe plug 105, the current through fifth zone 93 of ohmic material and through the 45-ohm voltage-divider resistor jumps upward to about 0.048 ampere, thereby generating about 2.16 volts across the resistor. This is more than adequate to turn on a transistor, and may be divided in half if desired. In FIG. 12, curve (E) represents the voltage across the ten-ohm resistor, while curve (F) represents the voltage across the 45-ohm voltage-divider resistor. It will be noted that both voltages subside and approach stability after the water in contact with the end of NPT pipe plug 105 has time to warm up and reach a steady-state temperature. Once again, a latching type of output indicator may be employed to record the fact that water has appeared in contact with the end of NPT pipe plug 105.

E. Clamp-On-Type Liquid Detector

Figure 11A:
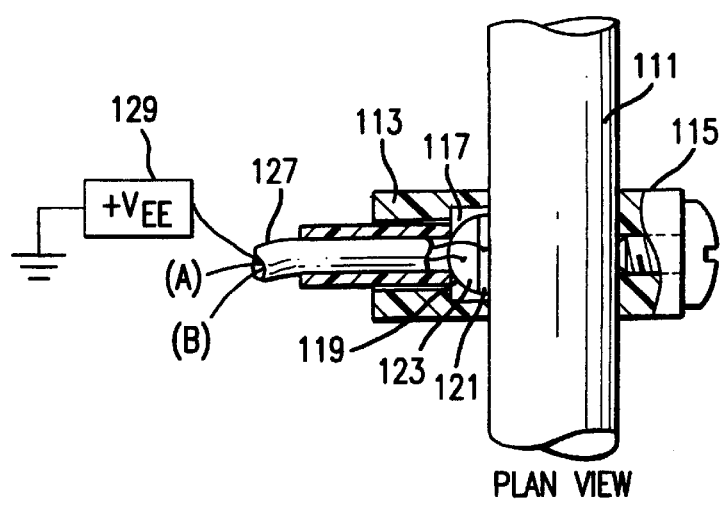
FIG. 11A is a plan view, partly in section, of a clamp-on-type liquid detector, mounted in a plastic fixture on a fluid conduit. The configurations of the PTC material and of the ohmic material are similar to those of FIG. 4, but the fluid conduit takes the place of the shallow diaphragm of FIG. 4.
Figure 11B:
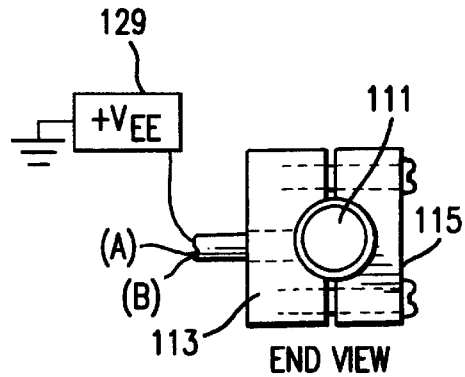
FIG. 11B is an end view, in section, of the liquid detector of FIG. 11A, showing the clamping arrangement.

Turning now to FIG. 11 A, we see a PTC sensor clamped to the outer surface of a pipe 111 by a first clamp member 113 and a second clamp member 115, which may be formed of plastic material. First clamp member 113 has a recess 117 with shoulders 119 which support the PTC sensor and urge it against the surface of pipe 111. The PTC sensor may be formed by dividing a 0.31-inch-diameter Keystone disk of PTC material into halves by sawing it along a plane that passes through the axis of the disk. One of the flat surfaces resulting from the sawcut is pressed against the surface of pipe 111. As in the configuration of FIG. 4, the ohmic material on one face of the disk of PTC material is divided by a cut made through that ohmic material about 0.05 inch away from the flat surface resulting from division of the disk. Thus, the ohmic material on one face of the PTC material is divided into an eighth zone 121 of ohmic material and a ninth zone 123 of ohmic material. On the opposite face of the PTC material is a tenth zone 125 of ohmic material which, in FIG. 11A, is concealed behind eighth zone 121 and ninth zone 123. Tenth zone 125 of ohmic material is connected by a wire which runs through a third cable 127 to a fifth source 129 of positive potential $+V_{EE}$.

Figure 13:
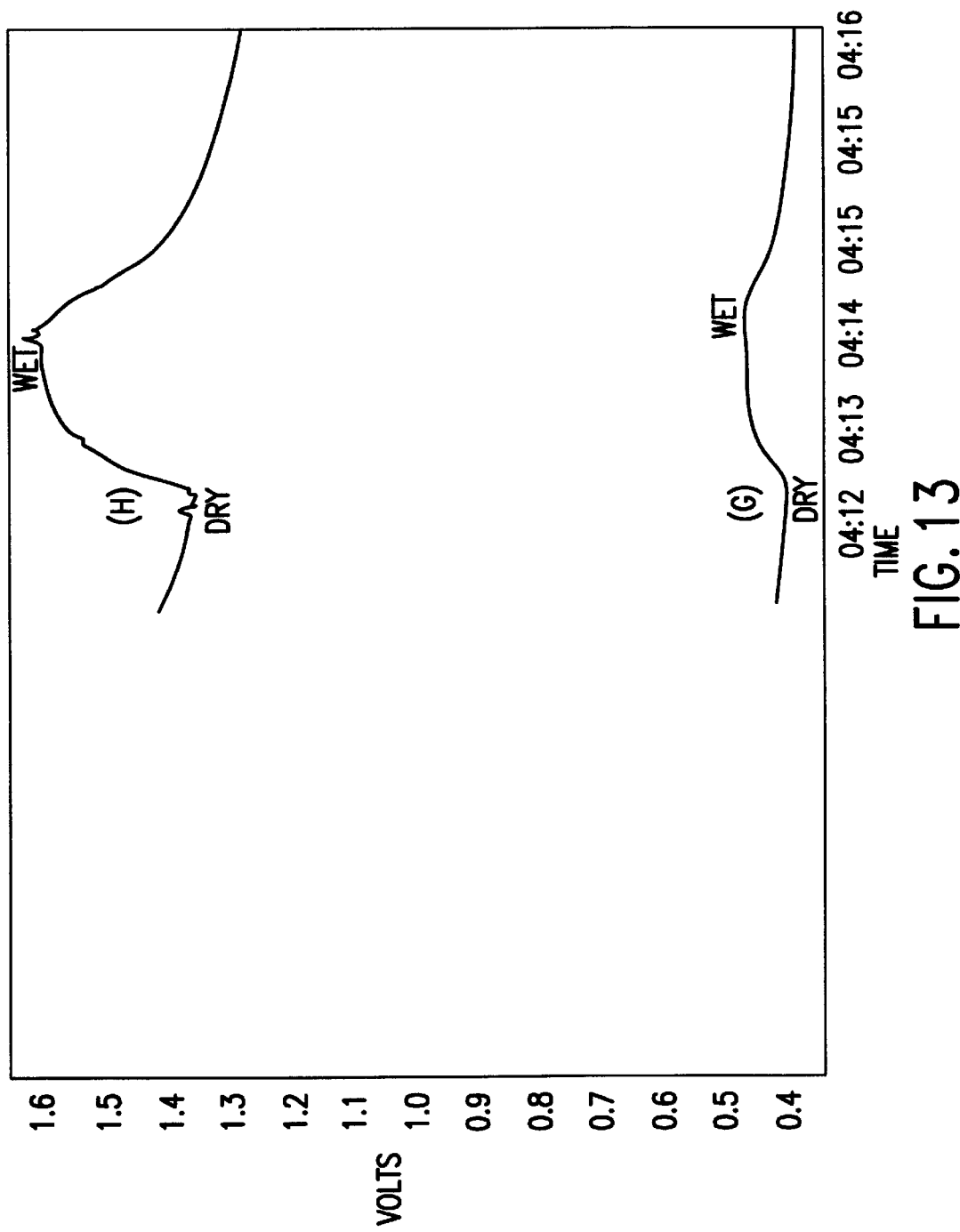
FIG. 13 is a fifth plot of respective voltages across resistor means in series with first and second zones of the second layer of ohmic material as functions of time as water begins to flow through the conduit of the clamp-on-type liquid detector illustrated in FIG. 11A and FIG. 11B.

Eighth zone 121 of ohmic material may be connected through a resistor of about 83 ohms to ground. This is merely a suggested value of resistance, and is not to be taken in a limiting sense. Ninth zone 123 of ohmic material may be connected through a resistor of about ten ohms to ground. When fifth source 129 of positive potential +$V_{EE}$, which may be about 24 volts, is applied to tenth zone 125 of ohmic material, there will occur the usual inrush of current that will generate voltage spikes much as shown in FIG. 12 but which do not appear in curves (G) and (H) of FIG. 13 because of late initialization of the timing when those curves were recorded. The respective voltages across the 83-ohm resistor and the ten-ohm resistor were on their way to stabilization in the "dry mode" when water suddenly appeared in pipe 111. Upon the appearance of room-temperature water in pipe 111, the current through the 83-ohm resistor increased from 0.017 ampere to 0.022 ampere, thereby generating a temporary voltage surge of 0.415 volt. Curve (H) in FIG. 13 shows a slightly smaller temporary voltage surge. If this surge is superimposed upon the bias voltage of an NPN transistor, the voltage surge is sufficient to turn on an NPN transistor and operate an alarm or other output circuit.

In FIG. 13, the voltage across the 83-ohm resistor appears to be headed for a stabilization level which is lower after the temporary voltage surge than before it. This fact can be explained by the observation that there is no mention that the water which appeared in pipe 111 is moving. Accordingly, the heat transferred to the water by the sensor warms the water to a temperature higher than room temperature, thereby moving the operating point of the PTC material upward on the curve to a condition of higher resistance.

F. Sensor and Control Circuit for Inductive Load

Figure 14A:
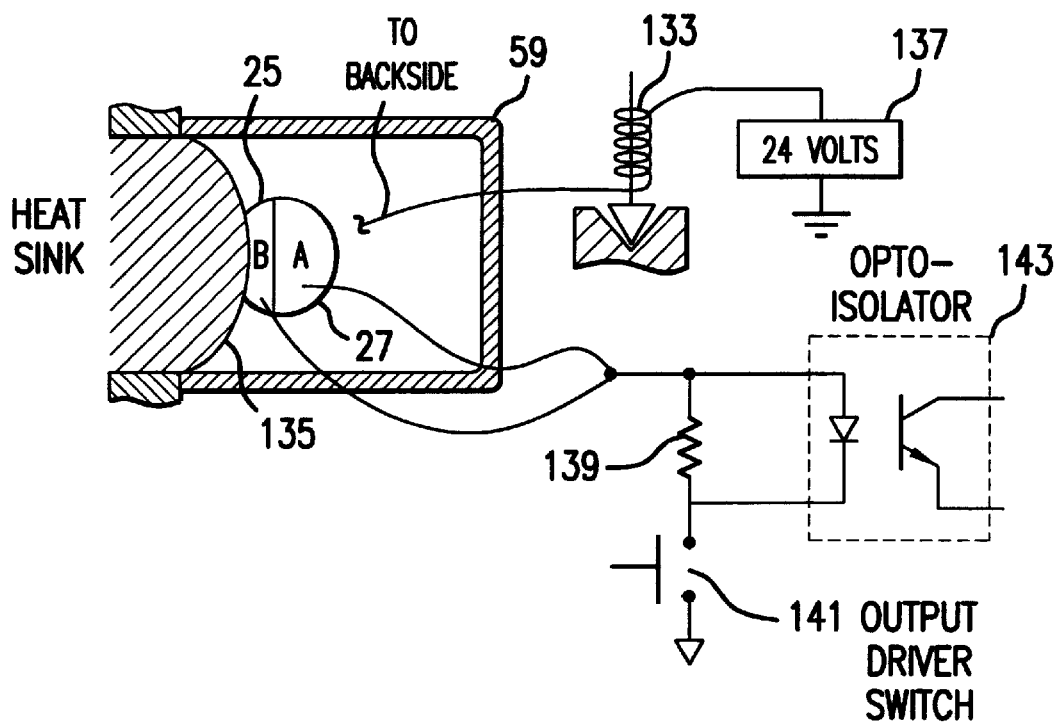
FIG. 14A is a schematic representation, partly in section, of a sensor and control circuit especially adapted for driving an inductive load such as a solenoid in response to the appearance of water, or other material having heat capacity, on the surface of a diaphragm or other thin membrane.
Figure 14B:
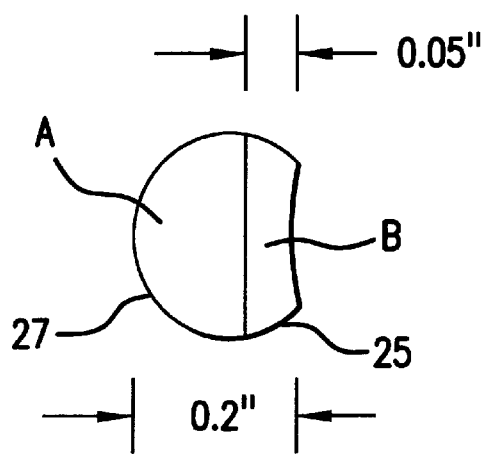
FIG. 14B is a plan view of a sensor for the configuration of FIG. 14A, giving suggested typical dimensions for the sensor.

Turning finally to FIG. 14A of the drawings, we see a sensor and control circuit especially adapted for driving an inductive load, such as a solenoid valve, in response to the appearance, or non-appearance, of water or other substance characterized by substantial heat capacity. The water may appear, or not appear, in contact with a thin diaphragm or membrane, as shown in FIG. 14A, or it might appear, or not appear, in a fluid conduit 65 such as the one illustrated in FIG. 6 of the drawings.

If a solenoid valve 133 is intended to turn on water which will then flow past a second diaphragm 135, it will be important to know whether water is actually flowing past second diaphragm 135 as a result of the opening of solenoid valve 133. In some applications where it is critical to determine that water flow has been initiated, a discrete flow sensor or valve-position indicator is employed to verify that the flow transition has indeed taken place. However, the additional flow sensor or valve-position indicator adds to the cost and complication of the valve-control circuitry. Accordingly, the present invention makes it possible to verify the flow transition by using a simple extension of the circuitry that controls the solenoid valve.

For this application, one may employ somewhat more than half of a Keystone RL 3006-50-7025-PTO disk which has been shaped to have one concave edge, rather than the convex edge of the PTC sensor illustrated in FIG. 4. However, the similarities are such that we shall again refer to "first zone 25 of ohmic material" and "second zone 27 of ohmic material" on one face of the tablet 21 of PTC material. On the other face of the tablet, of course, is "first layer 23 of ohmic material," which is concealed from view in FIG. 14A and FIG. 14B. In the configuration of FIG. 14A, first layer 23 of ohmic material is connected by a wire to one terminal of the coil of solenoid valve 133. The other terminal of the coil of solenoid valve 133 is connected to a sixth source 137 of positive potential $V_{FF}$, which again may be about 24 volts.

First zone 25 of ohmic material and the portion of tablet 21 proximate thereto are pressed against second diaphragm 135 and may be secured thereto by a thin layer of thermal epoxy. In this application, both first zone 25 of ohmic material and second zone 27 of ohmic material are connected to a first terminal of a read-out resistor 139 whose second terminal is connected through an output-driver switch 141 to ground. An optoisolator 143 may be connected across first and second terminals of read-out resistor 139 to prevent any extraneous signal from being fed back to the PTC sensor comprising tablet 21 and its facing layers of ohmic material. As shown in FIG. 14B, the cut made through one facing layer of ohmic material to separate first zone 25 from second zone 27 may be positioned about 0.05 inch from the chord across the concave edge of tablet 21. The cut may be located about 0.2 inch from the remote edge of second zone 27 of ohmic material. The sensor may be mounted in a container 59, with leads brought out individually or preferably combined in a cable through the wall of container 59, which may comprise a plastic cup. A groove may be formed around the inner surface at the mouth of container 59 to receive the periphery of second diaphragm 135. Water flowing through solenoid valve 133 may be guided past the surface of second diaphragm 135 remote from the sensor. When the sensor and diaphragm have been installed in container 59, the remaining space within the container may be filled with rigid foam 63.

When output driver switch 141 is closed, there will be an initial surge of current from sixth source 137 through the coil of solenoid valve 133 and thence through the sensor and read-out resistor 139 to ground. The initial surge may be about 0.25 ampere because both portions of tablet 21 of PTC material are in their low-resistance state. However, the portion of tablet 21 proximate second zone 27 of ohmic material very quickly heats up past its Curie temperature and assumes the high-resistance state. Accordingly, the current through read-out resistor 139 drops to or below 0.10 ampere, depending upon the state of resistance of the portion of tablet 21 proximate first zone 25 of ohmic material. If solenoid valve 133 has successfully turned on the water flow past second diaphragm 135, the current through read-out resistor 139 remains at or about 0.10 ampere because the portion of tablet 21 in contact with second diaphragm 135 is still in its low-resistance state. However, if no water is present or flowing past second diaphragm 135, the entire tablet 21 assumes its high-resistance state, and the current through read-out resistor 139 decreases to about 0.05 ampere.

When the portion of tablet 21 proximate first zone 25 of ohmic material—and proximate second diaphragm 135—changes from its low-resistance state to its high-resistance state, or vice versa, the change in voltage across read-out resistor 139 is approximately 1.25 volts. This voltage change is easily detected by optoisolator 143, whose output signal may be used to operate an alarm or initiate a test cycle on solenoid valve 133. The PTC sensor also acts as a protective device for solenoid valve 133. If the coil of the valve should become "short-circuited," the entire tablet 21 of PTC material would assume its high-resistance state and would limit the current flowing through the sensing circuit. Again, if the valve fails to open, and if there is no water flowing past second diaphragm 135, the entire tablet 21 will assume its high-resistance state and will prevent the coil of solenoid valve 133 from overheating.

Although full disclosure and discussion of the various aspects of the apparatus and operation thereof in accordance with my invention have been presented in the foregoing paragraphs, it is possible that certain variations thereof can be made in the future without departing from my invention. Accordingly, the scope of my invention is defined in the following claims, which cover the elements of my invention and equivalents thereof.

We claim:

1. A sensing and switching circuit comprising:
   (a) a body of positive-temperature-coefficient material having a first conductive coating on a first surface thereof and a second conductive coating on a second surface thereof, said second conductive coating being divided into a first zone and a second zone which are not in direct electrical contact with each other,
   (b) a source of first electric potential connectable to said first conductive coating,
   (c) first resistive means for connecting said first zone of said second conductive coating to a source of second electric potential different from said first electric potential, said first resistive means having first and second terminals and a node intermediate said first and second terminals,
   (d) second resistive means for connecting said second zone of said second conductive coating to a source of electric potential different from said first electric potential,
   (e) first switching means for connecting said source of first electric potential to said first conductive coating,
   (f) means for thermally coupling said first zone of said second conductive coating, and the portion of said body of positive-temperature-coefficient material proximate thereto, to a heat receptor, and
   (g) output switching means coupled to said node.

2. A sensing and switching circuit in accordance with claim 1 in which said output switching means is a transistor.

3. A sensing and switching circuit in accordance with claim 1 in which said output switching means is an NPN transistor having its base coupled to said node.

4. A sensing and switching circuit in accordance with claim 3, further including indicating means connected to the collector of said NPN transistor.

5. A sensing and switching circuit in accordance with claim 1 in which said first switching means is adapted for intermittent operation.

6. A sensing and switching circuit in accordance with claim 1 in which said thermal coupling means is a diaphragm in contact with said first zone of said second conductive coating and said portion of said body of positive-temperature-coefficient material proximate thereto.

7. A sensing and switching circuit in accordance with claim 6 in which said diaphragm is bonded to said first zone of said second conductive coating and to said portion of said body of positive-temperature-coefficient material proximate thereto.

8. A sensing and switching circuit in accordance with claim 5, further including a clock for controlling the operation of said first switching means.

9. A sensing and switching circuit in accordance with claim 1, further including a supporting matrix of rigid foam.

10. A sensing and switching circuit in accordance with claim 9 in which said rigid foam is characterized by substantial thermal conductivity.

11. A sensing and switching circuit in accordance with claim 9, further including a receptacle surrounding and retaining said rigid foam.

12. A sensing and switching circuit in accordance with claim 1, further including a hollowed-out pipe plug for supporting said circuit within its hollowed-out portion.

13. A fluid detector comprising:
    (a) a conduit for said fluid,
    (b) a thermally-conductive ring at least partially encircling said conduit,
    (c) a body of positive-temperature-coefficient material having a first conductive coating on a first surface thereof and a second conductive coating on a second surface thereof, said second conductive coating being divided into a first zone and a second zone which are not in direct electrical contact with each other,
    (d) said first zone of said second conductive coating being in contact with said thermally-conductive ring,
    (e) said second zone of said second conductive coating being in contact with said conduit at a point displaced from said ring along the axis of said conduit,
    (f) first resistive means, having two terminals and a node intermediate its terminals, for connecting said first zone of said second conductive coating to ground,
    (g) second resistive means for connecting said second zone of said second conductive coating to ground, and
    (h) means for electrically energizing said first conductive coating.

14. A fluid detector in accordance with claim 13, further including output switching means connected to said node of said first resistive means.

15. A fluid detector in accordance with claim 14 in which said output switching means is a transistor.

16. A fluid detector in accordance with claim 14, further including an annunciator coupled to the output terminals of said output switching means.

17. A fluid detector in accordance with claim 13, further including a container surrounding said body of positive-temperature-coefficient material on said conduit.

18. A fluid detector in accordance with claim 17, further including rigid foam in the space between said body of positive-temperature-coefficient material and said container.

19. A fluid detector in accordance with claim 18 in which said rigid foam is characterized by substantial thermal conductivity.

20. A sensing and switching circuit for an inductive load comprising:
    (a) a body of positive-temperature-coefficient material having a first conductive coating on a first surface thereof and a second conductive coating on a second surface thereof, said second conductive coating being divided into a first zone and a second zone,
    (b) a source of first electric potential connectable through said inductive load to said first conductive coating,
    (c) resistive means having first and second terminals for connecting said first zone and said second zone of said second conductive coating to a reference potential different from said first electric potential,
    (d) first switching means for closing the electrical path from said source of first electric potential through said inductive load, said body of positive-temperature-coefficient material, and said resistive means to said reference potential different from said first electric potential, and
    (e) output switching means connected between said first and second terminals of said resistive means.

21. A sensing and switching circuit in accordance with claim 20 in which said output switching means includes a transistor.

22. A sensing and switching circuit in accordance with claim 21 in which said output switching means further includes an optoisolator.

23. A sensing and switching circuit in accordance with claim 20, further including means for thermally coupling said first zone of said second conductive coating, and the portion of said body of positive-temperature-coefficient material proximate thereto, to a heat receptor.

24. A sensing and switching circuit in accordance with claim 23 in which said thermal-coupling means is a diaphragm.

25. A sensing and switching circuit in accordance with claim 24 in which said diaphragm is bonded to said first zone of said second conductive coating and to the portion of said body of positive-temperature-coefficient material proximate thereto.

26. A method for sensing and announcing the presence of a fluid in contact with a heat-conductive structure which comprises the steps of:

(a) providing in thermal contact with said heat-conductive structure a body of positive-temperature-coefficient material having on its first surface a first conductive coating and on its second surface a second conductive coating divided into a first zone and a second zone, only the first zone being in thermal contact with said heat-conductive structure, (b) electrically energizing said first conductive coating, (c) sensing the voltage across at least a portion of a first resistance connected between ground and said first zone of said second conductive coating, (d) feeding said sensed voltage to a switching device adapted to turn on in response to a predetermined level of positive voltage, (e) recording the instant of time when said switching device turns off, (f) measuring the elapsed time between turn-on and turn-off of said switching device, (g) periodically repeating steps (b) through (f) until an occurrence when said elapsed time between turn-on and turn-off increases, and (h) noting the time of said occurrence as the time of appearance of fluid in contact with said heat-conductive structure.

27. A method in accordance with claim 26, further including the step of giving an alarm following said occurrence.

* * * * *